United States Patent
Auvray et al.

(10) Patent No.: US 9,713,451 B2
(45) Date of Patent: Jul. 25, 2017

(54) REAL-TIME DISPLAY OF VASCULATURE VIEWS FOR OPTIMAL DEVICE NAVIGATION

(71) Applicant: KONINKLIJKE PHILIPS N.V., Eindhoven (NL)

(72) Inventors: Vincent Maurice Andre Auvray, Meudon (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 14/370,243

(22) PCT Filed: Jan. 4, 2013

(86) PCT No.: PCT/IB2013/050088
§ 371 (c)(1),
(2) Date: Jul. 2, 2014

(87) PCT Pub. No.: WO2013/102880
PCT Pub. Date: Jul. 11, 2013

(65) Prior Publication Data
US 2014/0371578 A1    Dec. 18, 2014

(30) Foreign Application Priority Data
Jan. 6, 2012  (EP) .................................. 12305015

(51) Int. Cl.
*A61B 6/12* (2006.01)
*A61B 34/20* (2016.01)
(Continued)

(52) U.S. Cl.
CPC ............... *A61B 6/12* (2013.01); *A61B 6/463* (2013.01); *A61B 6/481* (2013.01); *A61B 6/485* (2013.01);
(Continued)

(58) Field of Classification Search
CPC ......... A61B 6/12; A61B 6/485; A61B 6/5229; A61B 6/487; A61B 6/463; A61B 6/503;
(Continued)

(56) References Cited

U.S. PATENT DOCUMENTS 6,322,509 B1 * 11/2001 Pan ...................... A61B 5/1075
                                                    600/443
8,509,511 B2 * 8/2013 Sakaguchi ............... A61B 6/12
                                                    382/131
(Continued)

FOREIGN PATENT DOCUMENTS

JP    2005087633 A    4/2005
JP    2011156321 A    8/2011
(Continued)

OTHER PUBLICATIONS

C. Chalopin, et al., "Modeling the 3D Coronary Tree for Labeling Purposes", Medical Image Analysis 5 (2001), pp. 301-315.
(Continued)

*Primary Examiner* — Peter Luong

(57) ABSTRACT

An apparatus configured to generate for display a plurality of vasculature views alongside a live fluoroscopy image. The views are selected in such a way that they allow visualizing the 3D structure of the vasculature segment in which the device is currently navigating. The view is best relative to one or a weighted average of a plurality of goodness of view standards. As the device progresses and new fluoroscopy images are acquired, the views are updated accordingly.

14 Claims, 2 Drawing Sheets

(51) Int. Cl.
 *A61B 6/00* (2006.01)
 *A61B 90/00* (2016.01)

(52) U.S. Cl.
 CPC .............. *A61B 6/487* (2013.01); *A61B 6/503* (2013.01); *A61B 6/504* (2013.01); *A61B 6/5229* (2013.01); *A61B 34/20* (2016.02); *A61B 90/37* (2016.02); *A61B 6/4441* (2013.01); *A61B 2034/2065* (2016.02); *A61B 2090/367* (2016.02); *A61B 2090/376* (2016.02)

(58) Field of Classification Search
 CPC ....... A61B 6/481; A61B 6/504; A61B 6/4441; A61B 90/37; A61B 34/20; A61B 2090/367; A61B 2090/376; A61B 2034/2065
 See application file for complete search history.

(56) References Cited

U.S. PATENT DOCUMENTS

| | | |
|---|---|---|
| 2004/0019264 A1 | 1/2004 | Suurmond et al. |
| 2007/0058781 A1 | 3/2007 | Nakano |
| 2007/0100223 A1 | 5/2007 | Liao et al. |
| 2010/0002839 A1 | 1/2010 | Yokota et al. |

FOREIGN PATENT DOCUMENTS

| | | |
|---|---|---|
| WO | WO2007113705 | 10/2007 |
| WO | 2011039673 A1 | 4/2011 |
| WO | WO2011086475 | 7/2011 |

OTHER PUBLICATIONS

J.T. Dodge, et al., "Intrathoracic Spatial Location of Specified Coronary Segments on the Normal Human Heart; Applications in Quantitative Arteriography, Assessment of Regional Risk and Contraction, and Anatomic Display", Circulation 1988; 78, pp. 1167-1180.

J.T. Maddux, et al., "Rotational Angiography and 3D coronary Modeling: Revolutions in the Cardiac Cath Lab", Medicamundi, Philips Medical Systems, Shelton, CT, US, vol. 47, No. 2, Aug. 1, 2003, pp. 8-14.

* cited by examiner

REAL-TIME DISPLAY OF VASCULATURE VIEWS FOR OPTIMAL DEVICE NAVIGATION

CROSS-REFERENCE TO PRIOR APPLICATIONS

This application is the U.S. National Phase application under 35 U.S.C. §371 of International Application Ser. No. PCT/IB2012/050088, filed on Jan. 4, 2013, which claims the benefit of European Application Serial No. 12305015.5, filed on Jan. 6, 2012. These applications are hereby incorporated by reference herein.

FIELD OF THE INVENTION

The present invention relates to an apparatus for aiding in navigating a device in a network of tubular structures, to a method for aiding in navigating a device in a network of tubular structures, to a medical x-ray imaging support system, to a computer program element, and to a computer readable medium.

BACKGROUND OF THE INVENTION

During a PCI (Percutaneous Coronary Intervention) a guide-wire is introduced in and advanced along cardiac vessels to support treatment of cardiac stenosis.

When navigating in the vessels, the clinician relies on a static image of the vasculature shown next to a live fluoroscopic image.

The vasculature image typically depicts the vessels from the same perspective as the fluoroscopic image. However, the 3D vasculature geometry is complex, and at times difficult to represent.

WO 2011/086475 describes a system for navigating an interventional device.

SUMMARY OF THE INVENTION

There may therefore be a need for a different system to support a clinician during an intervention.

The object of the present invention is solved by the subject matter of the independent claims wherein further embodiments are incorporated in the dependent claims.

It should be noted that the following described aspects of the invention equally apply to the method of aiding in navigating a device in a network of tubular structures, to the medical x-ray imaging support system, to the computer program element and to the computer readable medium.

According to one aspect of the present invention there is provided an apparatus for aiding in navigating a device in a network of tubular structures. The apparatus comprises:
  an input unit configured to receive a current reference or "lead" projection image acquired at a first projection direction whilst the device is residing in the network of tubular structures, the projection image showing, when displayed, a footprint of the device;
  a processing unit configured to use a current in-image position of the footprint and a model of the network to retrieve at least one supplementary projection image from a sequence of previously acquired 2D projection images. The so retrieved supplementary image shows, when displayed, at least a partial footprint of the network and the so retrieved supplementary image affords a view along a second projection direction on the network at a section of interest where the device currently resides;
  a graphics display generator configured to generate for display on a screen a graphics panel including the current projection image and the supplementary projection image. The apparatus is configured to update the graphics panel upon receipt of a new projection image at the input unit, the updated panel then including the new projection image and a newly or subsequently retrieved supplementary projection image.

According to one embodiment the network of tubular structures is the cardiac vasculature and the reference projection image is a (live) fluoroscopic ("fluoro") image from among a plurality of fluoroscopic images acquired one at a time during the course of a PCI (Percutaneous Coronary Intervention). The device may be a guide-wire advanced through the vasculature by a clinician to navigate to a lesion in a particular branch of the vasculature.

According to one embodiment the sequence of supplementary projection images are angiographies ("angios") of the vasculature, each encoding a different footprint of the vasculature. The angiographies were acquired previously to the intervention and/or operation of the apparatus. The 2D image information as encoded in the angiographies is harnessed to supplement in real-time each one of the fluoro images acquired during the intervention.

In other words, the apparatus operates to display a number of vasculature views chosen in such a way that they allow best visualizing the 3D structure of the vessel segment in which the device is currently navigating. The views are adapted automatically so that the current vessel section of interest for the purpose of navigation is as well defined at all times throughout the intervention. In yet other words, the apparatus collates and prepares for display for the clinician relevant spatial information to so foster better understanding of the 3D structure of the locale where the vessel is currently navigating. The selection of views is based on or guided by the view on the in-situ position of the guide-wire as per the current fluoro image whose acquisition the clinician requests as her or she sees fit throughout the course of the intervention.

In conclusion, the apparatus detects the navigating device in the fluoroscopic image, and computes the device's position in the vasculature to so identify the vascular section of current interest. Once the current vascular section of interest is gotten, optimal views are selected that allow assessing the local 3D geometry at the point in the vasculature where the device is currently residing.

The apparatus when in operation relies solely on 2D image information. 3D image calculations during run-time are not involved which helps reduce CPU time thereby ensuring responsiveness and enhanced real-time performance. In particular, no (CT) 3D image volume acquisition is needed which helps keep down both, intervention time and X-ray radiation exposure thus benefiting the patient. This also simplifies the workflow since no intra-operational 3D data is to be acquired.

According to one embodiment, the model is generic so is not computed from the particular tubular network considered.

According to one embodiment, the vasculature model is one from a collection of different models each corresponding to one of the cardiac phases. The processing unit configured to select the network model to correspond to the shape of the vasculature during acquisition time of the current projection image. This allows accounting for the cardiac dynamics because the vasculature which surrounds the heart muscle changes it shape or is distorted as the muscle alternately contracts and expands.

According to one embodiment the plurality of (previously acquired) 2D projection images have been acquired along different projection directions. The second projection direction of the supplementary image affords a better view on the network at the section of interest than another projection image from among the sequence when measured against one of a plurality of different goodness of view standards or a combination of the plurality of different goodness of view standards.

The standard or the plurality of standards accounts for any one of the following or a combination or average thereof:

(i) low degree of overlaps in the part of the footprint representing the section of interest, (ii) low degree of foreshortening of the part of the footprint representing the section of interest, (iii) high degree of tortuosity of the part of the footprint representing the section of interest. The processing unit configured to compute, based on the network model, a score for the goodness of view standard. The "better" view may be better than all of the angios in the sequence ("best view") or may better than a true subset of angios from among the sequence, the later being in particular the case when retrieving angio having a score higher than a user adjustable threshold score or value. "Low" or "high" goodness of standard view standard scores mean either a particular score of one angio being higher than the score of another angio or that the score a particular angio is higher or lower than the threshold score.

Using a weighted average to combine the different standards of overlap, foreshortening and tortuosity allows finding a compromise or strike the right balance between these viewing standards to better account for the clinician's needs when carrying out the intervention. Other ways of combination are also contemplated such as maximum, median, non-linear mixing.

According to one embodiment, the processing unit is configured to retrieve along with the supplementary image a reference supplementary image. The reference supplementary image has substantially the same projection direction as the current reference projection image and the supplementary projection image is computed to afford a better view on the network at the section of interest than the reference supplementary image when measured against the first/ user-selectable goodness of view standard. In other words, the supplementary image and the reference supplementary image together afford complimentary views on the section of interest. In this way the collection of projection directions of the retrieved supplementary projection images form a more informative sample of views around the region of interest because the perspective chosen by the operator in relation to the device can be accounted for. This allows promoting a better understanding of the vasculature's 3D structure thereby helping the clinician to navigate the vasculature quicker.

According to one embodiment complimentary views are achieved by the processor retrieving along with the supplementary image at least one further supplementary image so that a group of supplementary projection images are retrieved. The further supplementary image affords a better view on the network at the section of interest than the supplementary image when measured against a second goodness of view standard different from the first goodness of view standard. In one embodiment, the group includes the reference supplementary image and there is at least one supplementary image that affords a better view than the reference supplementary image with respect to at least one of the plurality of standards.

According to one embodiment, the reference supplementary projection image is included into one pane of the graphics panel alongside with the complementary supplementary projection image shown in a further pane. In one embodiment, there is a default setting so that whenever the reference projection image is acquired, the supplementary reference projection is retrieved automatically.

According to one embodiment, the processing unit is configured to retrieve the new or subsequent supplementary projection image from images within a user-definable angular margin of the projection direction currently displayed supplementary projection image. In one embodiment retrieval within this pre-defined angular margin is implemented by using a further goodness of view standard ("angular closeness") score alongside with the standards mentioned above. A similar angular closeness goodness of view standard may also be enforced for supplementary projection images within a group. The supplementary projection images in the group or the subsequent supplementary projection images are encouraged to remain within a user-definably angular margin of projection directions of the previously retrieved supplementary projection image or images in the group. This angular closeness score may be defined by a decreasing function of the angular deviation between the supplementary projection images in the group or between the current supplementary projection image or images and the subsequent supplementary projection image or images to be retrieved. The lower the angular deviation the higher the corresponding angular closeness score, thus encouraging angular closeness in the score when combining with the other goodness of view scores. This allows providing to the user an enhanced visual experience with smooth transitions from a currently retrieved (and displayed) supplementary projection image and succeeding supplementary projection image retrieved (and displayed) throughout the course of the intervention.

According to another embodiment, rather than constraining retrieval/optimization to the angular margin around the projection direction of the current image, the smoothness of transition is achieved by briefly fading in and then out one image at a time from a sequence of sub-optimal projection images before the projection image with the best or better score is eventually being displayed. The sub-optimal images as determined during optimization have scores less than the best or better image and the sequence in which the images are faded in is determined according to their score, starting with the lower score gradually progressing through higher scores up to the better or best image having the highest score or a score above the optimization threshold. The sub-optimal images are stored in the order of their score in a buffer so they can be accessed in that order by the graphics display generator to effect their respective fade-in in the graphics panel. The number of so stored sub-optimal images and the duration of their respective fade-ins are user-definable to so allow tuning the apparatus for the best visual experience for the individual clinician.

According to one embodiment, the processing unit includes an optimizer configured to compute the goodness of view scores on which the retrieval is then based. The computation is either previously executed in a preparatory phase prior to operation of the apparatus (off-line mode) or is computed in real time upon retrieval (online mode).

According to one embodiment the graphics display generator is configured to use the current in-image position of the device to overlay a graphic representation of the device at a corresponding position in the supplementary projection image as included in the graphics panel or is configured to overlay on the reference projection image a graphic representation of the region of interest as shown in the supplementary projection image.

In one embodiment, the supplementary projection image is displayed against a flat background.

According to one embodiment the graphics display generator is configured to color code the region of interest in the supplementary projection image as included in the graphics panel. In other words, as the device is being progressed through the vasculature, the views are adapted to highlight the vascular section of interest in each of the retrieved supplementary images.

According to one embodiment the graphics display generator is configured to generate annotation information for display on the panel, the annotation information including the computed score for the goodness of view standard of the supplementary image and/or including one or more parameters used for the computation of the score. Further it will be understood by those skilled in the art that 2D images other than angios and/or fluoros may be used.

The invention may be put to use not only in the medical context of vascular interventions but also for other organs or may be put to use in non-destructive material testing of objects having a complex network of cavities. Probes may then be positioned by suitable guiding equipment at a desired location within the object otherwise inaccessible.

DEFINITIONS

Angiographies are 2D projection images taken after a contrast agent is resident in the network of tubular structure thereby conferring opacity to its tubular structure during X-ray image acquisition. In Fluoroscopy 2D projection images, no contrast agent is resident in the network of tubular structure so it is general only the guide-wire (and other radiation opaque matter such as bones, thick muscle tissue etc.) that is visible when the fluoroscopy image is displayed whereas the vasculature soft tissue is not discernible when the fluoroscopy image is displayed.

An "overlap" in a projection image taken along a projection direction is an image portion (usually discernible as clutter) that results from two or more of the tubular structures having their respective footprints intersecting in the image plane. In other words, at least one or of two or more tubular structures is spatially arranged either before or behind the other or others when viewed in that projection direction.

"View" and "projection" direction is used interchangeably herein.

BRIEF DESCRIPTION OF THE DRAWINGS

Exemplary embodiments of the invention will now be described with reference to the following drawings wherein:—

DETAILED DESCRIPTION OF EMBODIMENTS

Figure 1:
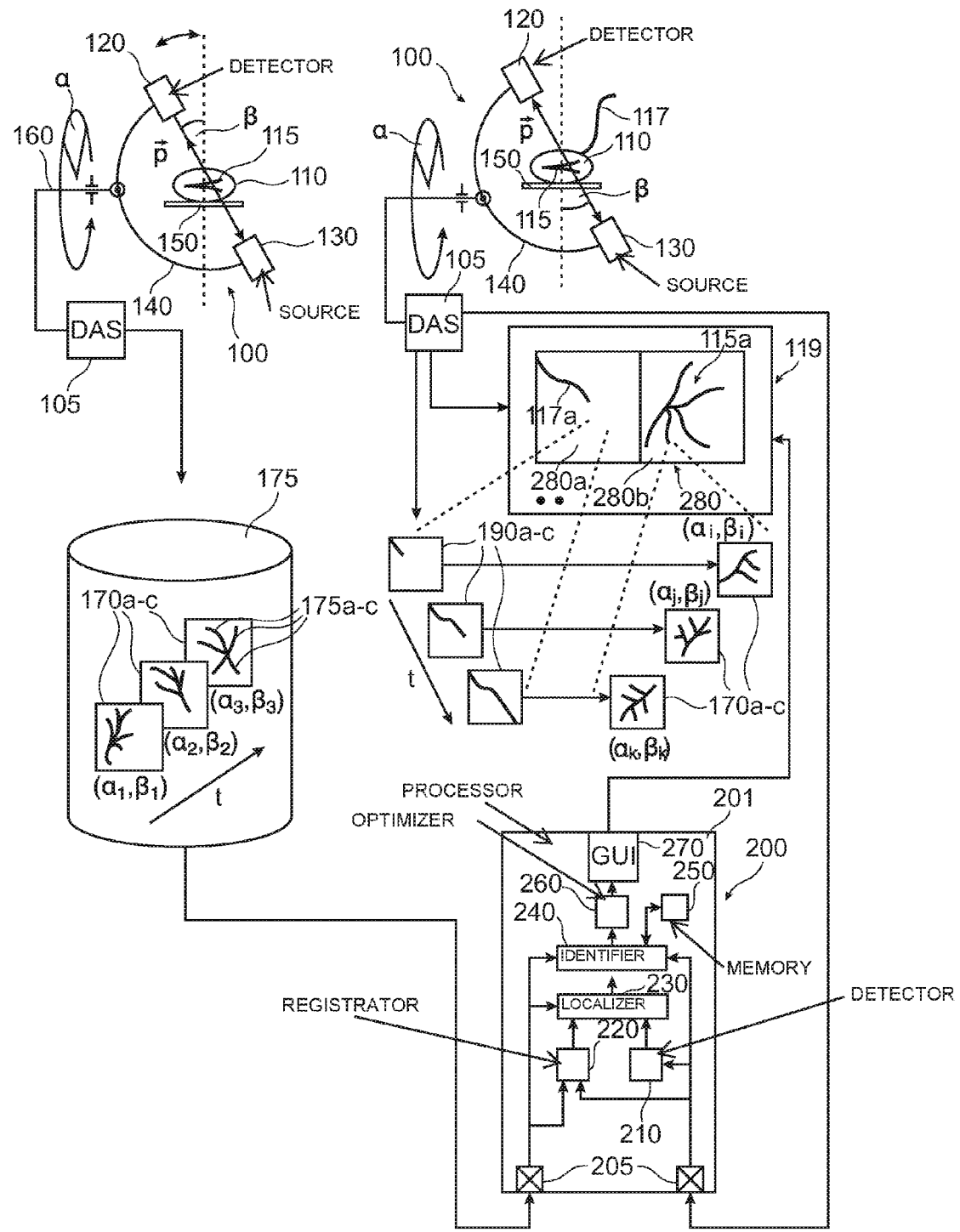
FIG. 1 shows a block diagram of an apparatus for aiding in navigating a device in a network of tubular structures.

To the left of FIG. 1 there is shown an x-ray imager 100 of the C-arm type. X-ray imager 100 is used in a preparatory planning phase to acquire a sequence of x-ray projection images 170a-c of an organ of interest to support in a later phase an intervention.

In one embodiment, the organ of interest is a patient 110's heart, in particular its coronary vasculature 115.

In the planning phase the patient is placed on an examination table 115. Imager 100 comprises a rigid C-arm structure 140 journaled on a bearing 160. Journaling allows rotation of C-arm 140 around a first axis passing through journaling 160. C-arm structure 140 can thus be positioned at various rotation angles • around vasculature 115. C-arm 140 is further rotatable around an axis perpendicular to the first axis to so assume different angulation angles • so that c-arm 140 enjoys at least 2 degrees of freedom.

C-arm 140 carries at one of its ends an x-ray source 130 and at the other end a detector 120 in opposed spatial relationship to x-ray source 130. The detector 120 includes an array of detector cells (not shown).

X-rays are emitted from x-ray source 130. The X-rays pass through vasculature 115 and are then detected at detector 120. The X-rays are formed from X-ray pencil beams p.

Each x-ray beam p is attenuated as it passes through the vasculature 115 and impact on same. It is this attenuated x-ray beam that is detected at detector 120.

The angle of incidence ("projection direction") at which the x-ray beam impacts vasculature 115 is defined by the pair (•, •) of rotation angle • and angulation angle •. The degree of attenuation experienced by each individual x-ray beam p depends on the type and amount of tissue the ray p is passing through. Each attenuated x-ray beam p impinges on a detector cell and generates there an electric signal anti-proportional to the degree of attenuation. The electric signal generated at each detector cell for an impinging x-ray beam p is then translated via data acquisition device 105 into a pixel value encoding a corresponding grey value. The pixel values are then stored in a matrix structure forming a projection image taken at a particular projection direction (•, •).

The sequence of projection images 170a-c is acquired during the image acquisition epoch, each individual projection image 170 a, b or c acquired generally along different projection directions. The sequence 170a-c of projection images of vasculature 115 is then stored on a data base 175. The projection images 170a-c may be stored in the DICOM format. The DICOM format includes meta-data encoding for each projection image the projection direction at which it was acquired along with its acquisition time t.

Vasculature 115 in itself has no radiation opacity meaning that the projection ("footprint") of vasculature 115 would not normally be visible in the projection images 170a-c. To remedy this, a contrast agent is administered to patient 110 prior to the image acquisition. Contrast agent accumulates in the vasculature 115 and so confers opacity to the vasculature. Because of the contrast agent, in each projection image 170a,b, or c (also known as angiographies) encodes a projection view or footprint 115a of the vasculature 115 along a different projection direction. The contrast agent carrying blood is flowing through those vessels and branching points, thereby dispersing the contrast agent throughout the vasculature down to its branches and sub-branches.

At the later intervention phase, the patient is still or again placed on the examination table 115 but this time no contrast agent is administered. One reason for the invention may be to treat a vascular stenosis, that is, a stricture in an inflicted vessel among the numerous vessels making up the cardiac vasculature 115. During the invention a guide-wire 117 is introduced into the vasculature and advanced through same. The goal is to position guide-wire 117 inside the inflicted vessel with its tip distal to the stricture so that balloons or stents can be slid along the guide-wire to be then positioned distal to the stenosis. After having placed the guide-wire, a balloon catheter can then be led along the guide-wire and placed at the stricture to then effect treatment thereof. In the intervention whilst the operator is advancing the guide-wire 117 through the vasculature, imager 100 is used to acquire in real-time (live) fluoroscopy images 190a-c one at a time of the vasculature 115 with the guide-wire 117 residing in same. The operator actuates a joy-stick provided at operator console 150 to position imager 100's c-arm 140 at a desired projection direction or angle and actuates a button or a pedal to have the fluoroscopy ("fluoro") projection image 190a-c acquired at that desired projection direction. Because no contrast agent is used during the intervention phase, each of the fluoro images 190a-c encode footprints 117a of the guide wire 117 but do not encode vasculature 115 footprints. In other words, when the fluoro images 190a-c are displayed the guide-wire footprint 117a is visible whereas the vasculature footprint 115a is not (or barely) visible.

In order to aid or support the surgeon in 3D navigation through the vasculature 115, apparatus 200 is used as shown at the lower right in FIG. 1.

The apparatus 200 comprises a processing unit 201. Processing unit 201 comprises a number of components: there is an input unit 205, a detector unit 210, a registrator 220, a localizer 230, an identifier 240, a (view-) optimizer 260, a memory 250 and a graphic display generator 270.

The components of the apparatus are shown as resident in processing unit 210. However, this is an exemplary embodiment only. The apparatus may instead be arranged in a distributed architecture and connected in a suitable communication network. In the illustrated embodiment the components are running as software routines on the processing unit 201. The components may also be arranged as dedicated FPGAs or as hardwired standalone chips. The components may be programmed in a suitable scientific computing platform such as Matlab® or Simulink® and then translated into C++ or C routines maintained in a library and linked when called on by processing unit 201.

Broadly speaking, apparatus 200 provides visual support for navigating the guide-wire 117 through the vasculature 115 by supplementing the 2D visual information content of the currently acquired fluoroscopy images 190a-c by using additional 2D image information from select ones of the 2D angiographies 170a-c recorded earlier.

A current one of the fluoroscopy images 190a-c along with the select one of the angiographies 170a-c are rendered for display by the graphic display generator 270 and displayed in a two-pane window 280 on a screen 119. In reference pane 280a the currently acquired fluoro image is shown, for example fluoro image 190a, and in supplementary pane 280b the selected one, angiography 170a say, from among the previously acquired angiography images 170a-c is shown.

The retrieved angiography 170a has been previously established by the apparatus 200 to afford a better view of the vasculature 115 than some or all of the other angiographies 170b-c held in storage 175. The optimized or better view is measured against one or more predetermined but selectable goodness of view standards.

As the operator advances the guide-wire 117a, a new fluoro image 190b is acquired. Apparatus 200 registers the change and then retrieves correspondingly updated angiography 170b and effects display of same alongside new fluoro image 190b.

In this manner, a dynamically updated sequence of displayed angiographies 170i-k is generated, each angiography so displayed supplementing the 2D image information as shown in the current fluoro image 190a-c.

The operation of apparatus 200 is now explained in more detail.

Operation

Apparatus 200 is in communication via a suitable communication network with imager 100's data acquisition system 105. Currently viewed fluoro image 190a is intercepted by apparatus 200 and fed into apparatus 200 via its interface input unit 205.

Interface unit 205 or a different interface unit allows accessing via the same or a different communication network the sequence of angiographies 170a-c held in data base 175.

The intercepted current reference fluoro image 190a is then passed on to localizer 210. Localizer 210 detects guide-wire footprint 117a in the image by using a suitable segmentation technique, for example pixel value thresholding. Localizer 210 then establishes the in-image position of guide-wire footprint 117a and records the position by a set of in-image position coordinates. For the purposes of establishing the position of the guide-wire it is understood that a reference point on the guide-wire footprint 117a is used, for example its end portion representative of guide-wire 117's tip. The end portion may be found by tracking pixel values and repeated pixel value thresholding.

The intercepted fluoro image 190a is then passed on to registrator 220. Registrator 220 then accesses the metadata associated with the sequence of angiographies 170a-c in data base 175 and uses the metadata to register the intercepted reference fluoro image onto the sequence of angiographies 170a-c. The registration results in the fluoro image 190a and the sequence of angiographies 170a-c being aligned along a common coordinate system.

In one embodiment the current fluoro is registered onto the angiography having the same (within a selectable margin) projection direction as the current fluoro image. The registration can be effected by matching or fitting guide-wire 117a in fluoro 190 to the vasculature footprint 115a in the angio 170a.

In one embodiment, the registration effected by registrator 220 also accounts for cardiac activity of the heart which imparts motion on vasculature 115. To this end apparatus 200 can be arranged with suitable interface means to receive an ECG signal to establish the current cardiac phase at the time of acquisition of current fluoro image 190a.

In other embodiments, the cardiac activity may be accounted for without ECG. For instance, when tracking the shape and motion of the guide-wire tip throughout the sequence of fluoros 190-a-c, one can filter the spatial position of this tip, so as to obtain the cardiac component that is a "beat" component approximating the human cardiac rate. From this filtered out beat component, the cardiac cycle may be inferred, and in particular the cardiac phase for image 190a may be inferred. In particular, the end diastole and end systole are the only two points in the cardiac cycle where the component indicates a null, that is, direction reverting motion. The same method can be applied on the angios 170a-c, using distinctive feature points on the vasculature (for instance vessel bifurcation points and the like). In addition, in the angios 170a-c, the general shape of vasculature allows an easier distinction between systole (general vessel tree contraction) and diastole (general vessel tree expansion).

The registration process involves computing a spatial transformation which effects aligning the sequence of angiographies 170a-c with the current fluoro image 190a. Contours of the guide-wire footprint 117a from one of the angiographies 170a-c is then projected onto the aligned fluoro image 190a to so obtain a pixel region representing the vasculature 115 in the fluoro image 190a. In-image coordinates describing this pixel region are then output to so form a "reference vasculature footprint".

According to one embodiment, a graphical overlay symbol representing the contours of the reference vasculature footprint is computed. The symbol is then overlaid on the fluoroscopic image to so effect what is known as a 2D cardiac road-mapping.

The coordinates of the reference vasculature footprint and the coordinates of the guide wire footprint 117 are now passed on from registrator 220 to localizer 230.

Localizer 230 uses the in-image position coordinates of the guide-wire footprint 117a and the reference vasculature footprint to obtain a position of the wire footprint 117a relative to and inside the reference vasculature footprint. This position inside the reference vasculature footprint then allows establishing in which anatomical part of the vasculature the device 117 is currently residing. Localizer 230 then access a medical database (not shown) and use a 2D (corresponding to the current projection direction) or a 3D generic model of the considered anatomy to translate the position of the guide-wire footprint inside the reference vasculature footprint into an identification label identifying the anatomical vasculature part, for example the main bifurcation between left main, LAD (Left Anterior Descending) and circumflex. Since the identification does not have the same resolution as the image data (the same label being shared by many pixels), a generic model, that is a non patient-specific anatomy description, is sufficient for the translation. The 3D generic model will be explained in more detail below in relation to operation of optimizer 260.

The position of the guide-wire footprint inside the reference vasculature footprint may be referred to as the (vascular) section of interest (SOI) footprint. The SOI footprint is that part of the vasculature footprint 115a that represents the vascular section of vasculature 115 where the guide wire 117 resided whilst the current fluoro image 190a was acquired. In other words, the SOI footprint is the identified part's footprint.

The identification label of the so identified anatomical part is then passed on as output from the localizer 230 to identifier 240.

Identifier 240 uses this identification label to establish the corresponding anatomical part across the sequence of angiographies 175a-c. For this purpose, the identifier 240 instructs registrator 220 to effect registration of the remaining angios 170b-c by using a generic model of the vasculature 115. Footprints of the projected 3D generic model are matched up with each of the vasculature footprints in the remaining angios 170b-c, each projection direction of each angio 170b-c defining a particular vasculature footprint corresponding to the 3D model projection in that direction. The respective vasculature footprints as encoded in each of the angiographies 175a-c can then be labeled. This labeling may also be executed in a previous phase when flow control passes from localizer 210 to registrator 220. In other words, each angiography is associated with a dictionary data structure suitable to resolve a pixel position inside the respective vasculature footprint into an identification label identifying the respective anatomical part of the vasculature.

For illustration, the identification labels for angiography 170c are shown as reference numerals 175a-c. The labels allow identifying by using the generic model of the anatomy (see below) one and the same anatomical part across the sequence of angiographies 170a-c, any one of the angiographies encoding a different view on the anatomical part.

In one embodiment the labeling of the anatomical parts across the sequence of angiographies 170a-c is executed previously after acquisition or is executed on demand when called on by the identifier 240. Preferably, labeling is executed previously to so enhance the real-time experience for the operator during intervention. A labeling algorithm is described in "Modeling the 3D coronary tree for labelling purposes", C. Chalopin et al, Medical Image Analysis 5 (2001), pp 301-315.

Identifier 240 then passes on to optimizer 260 the current projection direction of currently shown fluoro image 190a and the identification label for the anatomical part where the guide-wire 117 is currently residing and as established previously by localizer 230.

Optimizer 260 then uses the current projection direction and the identifier label to retrieve from the sequence of stored angiographies 170a-c the optimized views. Optimizer 260 computes an optimized projection direction and then retrieves from the sequence of stored angiographies 170a-c the one whose projection direction (•, •) has been computed as optimal with respect to a goodness of view standard.

According to one embodiment, optimizer 260 computes a goodness of view score of each available view corresponding to the different angiographies 170a-c and displays the best of the views 170a-c or a selectable one or for each goodness of view standard.

In one embodiment a view is considered "best" if its score is higher or as the case may be lower than a user pre-defined threshold value so that the "best view" is a collection of views each having a score higher or lower than the threshold value. If there are more than one "best" views, a random generator may be used to select the view to be displayed or the view is selected from among the collection so that its projection direction is closest to the currently displayed fluoro image 190a.

In the following a number of different goodness of view standards will be described and how optimizer 260 can be implemented to compute an optimized view with respect to each of those viewing standards or criteria. Optimizer 260 uses the formal model of the cardiac vasculature for the optimization.

According to one embodiment, the model is a labeled generic mean model of the coronary vasculature's geometry. Anatomical priors for the geometry of the coronary arteries are used and formalized into the mean geometric coronary model. The model can be stored in memory 250 as a suitable tree data structure with nodes linked by curvilinear segments. An example of vascular models can be found in J. Theodore Dodge et al "Intrathoracic spatial location of specified coronary segments on the normal human heart. Applications in quantitative arteriography, assessment of regional risk and contraction, and anatomic display", Circulation, 1988, 78, p. 1167-1180 or on p. 306, FIG. 5(b) in the Chalopin article referenced above. Anatomical priors are general non-patient-specific knowledge about to be expected image structures such as the general shape and number of vessels making up the vasculature or to take an example from human figure detection, an anatomical prior is the existence of a head and trunk and usually four limbs, etc.

A collection of such coronary models can be used, each according to the coronary dominance (right, balanced or left (this is the main characteristic), to the sex, to the age of the patient and to the different cardiac phases to so account for distortions of the vasculature during different cardiac phases.

Optimizer uses the labeling to map the SOI onto a model segment corresponding to the SOI, hereinafter called the "SOI segment". Prior to the mapping, optimizer selects the appropriate model to match the cardiac phase at acquisition time of the current fluoro 190a.

In one embodiment, prior to the mapping, the mean coronary tree can be adapted so that its projection over the different angiographies 170a-c correctly match each or a selection of the 2D segmented vessels in each or a sample selection of the angiographies 170a-c. The size of sample selection is user definable and may either be random or user-defined. In this way, the mean coronary tree can be calibrated which respect to the available sequence of angiographies 170a-c. This calibration or model registration is preferably effected in a preparatory phase prior to operation of apparatus 200.

Optimizer 260 then casts projection lines across the model passing through the SOI segment to so generate simulated projection views in an image plane. Each projection line represents one of the available views or projection direction of the sequence of angiographies 170a-c.

According to one embodiment, a goodness of view standard is defined by the SOI footprint (as indicted by the identification label) overlapping as few of the surrounding parts of the vasculature footprints as possible or by having overlap regions with less than a configurable threshold area value measured in a suitable square unit. This "low degree of overlap" standard can be implemented by keeping track of the how many segments the casted sample line intersects. The projection direction with the fewest or less than a user-definable number of intersections is then output as the best or better projection direction ("view"). The angiography that has been acquired at the so computed best or better projection direction is then retrieved from the sequence of angiographies 170a-c.

Another goodness of view standard is low degree of foreshortening in the SOI footprint. A low foreshortening standard may be enforced by tracking a longitudinal curve length of the projections of the SOI segment for different projection directions cast through the SOI segment. The length of the SOI segment projections are then compared with the real length of the SOI segment. The degree of foreshortening may be expressed as the ratio between projected lengths and the real length taken for each of the casted projection lines. Projection directions yielding a ratio within a user-definable margin of unity may then be output as a better or the best projection direction.

According to another embodiment a goodness of standard view is the degree of tortuosity of the SOI footprint. In this embodiment views are favored which show the SOI footprint in its more convoluted forms. This high degree of tortuosity standard can be implemented by computing for each projection line the mean of the mathematical curvature of the projection of the SOI segment along its length. Projection directions yielding the highest tortuosity score or a tortuosity higher than a user-definable threshold may then be output as a better or the best projection direction in respect of the high tortuosity standard. Optimizing with respect to the tortuosity standard allows focusing on angiographies with high information content for safe navigation in difficult because convoluted parts of the vasculature and to lay bare the geometry of those difficult locales.

Optimizer 260 is configured to establish the optimized view according to any one of the user selectable pre-defined goodness of view standards or is configured to establish the optimized view based on a weighted average or any combination of those pre-defined goodness of view standards. The weighted average combination or other combination allows negotiating a compromise if more than one standard is to be included in the computation. The weighted averaging or combination scheme may be implemented by mapping the above mentioned objective values (number or area of overlaps, length of foreshortenings, curvature) obtained in the computation to a common scoring scale. It is those scoring point on the scale that are then weighted by a factor ranging between naught and unity. The factor represents the importance which the clinician attaches to the respective standard. The user can then set a desired weighted average value deemed suitable in the clinical circumstances at hand. Optimizer 260 than optimizes to find projection directions yielding a weighted score within a definable margin of the set value.

In one embodiment, the optimizer is configured to execute above described optimizations not only for the SOI segment proper but for segments neighboring the current SOI segment. The user may specify by key stroke or mouse click a neighboring section, when the so retrieved angio is displayed in the graphics panel.

The optimizer can be configured to either compute the optimized views for each of the standards in a preparatory phase previous to operation of the apparatus 200. In an offline scenario, for each anatomical part and for each goodness of view standard, the best viewing directions can be recorded in a table. The table can be formed by a family of matrices with rows and columns, each entry indicating the range of best views in terms of (•, •) or only • or only • for the respective part (indicated in the row) and the respective standards indicated as per column. When operating in off-line mode, optimizer 260 then uses the identification label for the anatomical part of interest to look up for each of the desired standards the range of best views. Those ranges are then used to retrieve from among the sequence of angiographies 170a-c those angiographies whose projection direction falls into the respective range.

In a preferred embodiment, apparatus 200 is configured to compute the optimized views in real-time on demand during the operation of the apparatus.

According to one embodiment optimizer 260 is programmed to retrieve from among the sequence angiographies 170a-c a group of two or more angiographies that jointly afford a better or best view. The group of angiographies as determined by optimizer 260 are jointly optimized in that the retrieved group includes for each of the three or more viewing standards at least one angio that affords a best or better view with respect to that viewing standard. For example, one angio 170b in the group may afford a best view with respect to the low foreshortening standard but may not be best in the terms of the low overlap viewing standard. When optimizing jointly, optimizer 260 ensures that the so retrieved group includes at least on further angio 170c that complements angio 170b in that angio 170c is best with respect to the low overlap standard. In other words, optimizer 260 ensures that there is always one angio in the group that complements ("is complementary to") another angio in the group thereby compensating for the other angio's failure to satisfy any one of the viewing standards.

According to one embodiment, processing unit is configured to by-pass the optimization to retrieve either automatically for each current position of the guide-wire 117 a reference angiography having its projection direction aligned with the projection direction of the currently acquired and displayed fluoro image 190a. Alignment is within a user-definable deviation margin in case the current fluoro does not exactly match any of the available views. When a reference angiography is retrieved, optimizer is then configured so that the then retrieved and optimized angiography 170a is complementary for a user-selectable one of the viewing standards or that there is at least one angio in the optimized group of angios that is complementary to the currently retrieved reference angio. If at any given time during the intervention no reference angio is retrieved and the operator then requests one, the currently retrieved optimized angio or the group of complementary angios are re-computed to ensure complementarity with the now requested reference angio. In one embodiment, if requested by the user, the group also includes angios complementary with respect to the segments neighboring the SOI segment. In this embodiment, the group of angios includes at least one angio which affords a best or better view on the neighboring segment with respect to at least one of the viewing standard.

As the operator changes the position of guide-wire 117 and a new fluoro image 190b is acquired encoding a new in-image position of the guide-wire footprint, the apparatus takes this new guide-wire footprint as a new input translates it into a new SOI to update and re-compute a new optimized angio or group of angios as set out above. In this dynamic fashion, with the sequence of fluoros 190a-c acquired during the intervention a corresponding sequence of optimized angiographies 170i-k is then retrieved one or more at a time for display. This correspondence is indicted in the right hand side of FIG. 1 by the set of left-to-right arrows. Optimizer 260 ensures that the projection direction of the sequence of retrieved angiographies 170a-c provides at all times during the intervention the best or better joint information about the SOI.

The angiography 170a-c or the group of angiographies affording the optimized view or jointly optimized views as computed by optimizer 260 is or are then retrieved from database 175 and passed on to graphics display generator 270 to render for display the retrieved angiography or group of angiographies. The so retrieved best or better angiography or the group of complementary angios is/are then displayed in supplementary pane or panes 280b on screen 119 (in the FIG. 1 there is only on supplementary pane 280b shown) thereby replacing the previously computed and displayed angiography.

According to one embodiment viewing pane 280 includes two panes as shown in the embodiment in FIG. 1, that is, the reference pane 280a for the current fluoro image 190a and supplementary pane 280b showing the angiography whose projection direction has been computed by optimizer 260 to satisfy the currently selected goodness of view standard or satisfies a combination of all the goodness of view standards.

According to another embodiment panel 280 includes two or more supplementary viewing panes each pane displaying an angiography from among the retrieved group of angiographies affording the complementary views with respect to the any on the viewing standards.

In a preferred embodiment, the graphics panel includes a dedicated pane for the reference angio aligned with the currently displayed fluoro 190a. In this case, the optimized and displayed angio or group of angios is or are complementary to the reference angio.

According to one embodiment, the goodness of view and or the objective values used in the respective optimization are displayed in the respective pane 280a,b alongside the displayed projection image 170a,b.

According to one embodiment, simple user interaction means (not shown in FIG. 1), are provided to allow the user to quickly select one of the displayed angio views, thereby effecting automatically acquisition of a new fluoro image at the projection direction of the selected angio view. The complementary of the views afforded by the group of angios and the annotation information (such as the goodness of view scores) provided on the viewing panes helps the user to choose the most appropriate interventional fluoro view at a given instant of the intervention. In one embodiment, the interaction means is by having the panes arranged as GUI widgets responding to mouse click to effect the acquisition of the new fluoro then aligned with the projection direction of the clicked on pane 280a,b including the angio.

According to one embodiment, viewing graphics panel pane 280 is split up in separate panes each positionable across screen 119 as desired by the user. Alternatively, the viewing pane may be distributed across more than one screen, one or more panes displayed on each of the plurality of screens. In one embodiment the retrieval of the angiographies 117a-c are controlled so as to effect for the viewer a smooth transition between the subsequently retrieved and displayed angiographies. This impression of smooth transition can be implemented by sequentially fading-in briefly in the same viewing pane, suboptimal angiographies and displaying same with duration of display for each sub-optimal angio. The duration is the longer the closer their respective goodness of view is to the optimal one. Eventually, after a sequence of briefly displayed sub-optimal angio the optimal angio is then displayed.

Smoothness of transition may also be put into practice by having optimizer 260 enforce a further goodness of view standard defined in terms of angular closeness. In this embodiment, optimizer 160 constrains optimization with respect to overlap, foreshortening, and tortuosity to a user-definably angular region around the currently displayed angiography.

Any subsequently retrieved and displayed optimized angios must then have their projection direction within this angular region.

According to one embodiment, smoothness of transition is enforced by adding a further goodness of view standard in terms of angular closeness across the projection directions of subsequently retrieved angios 170i-k. The projection directions of previously retrieved angios are tracked and are used to control optimization in subsequent angio retrievals. In other words, a subsequent angio 170k is encouraged to remain within a user-definably angular margin of projection directions of the previously retrieved angios 170i-j. This angular closeness goodness of view score is used alongside with the other goodness of view standards (overlapping, foreshortening, tortuosity mentioned above. This angular closeness score may be defined by a decreasing function of the angular deviation between the angios 170b in the group or between the current angio 170i or angios and the subsequent angio 170j-k or angios to be retrieved. The lower the angular deviation the higher the corresponding score, thus encouraging angular closeness in the score when combining with the other goodness of view scores.

Figure 2:
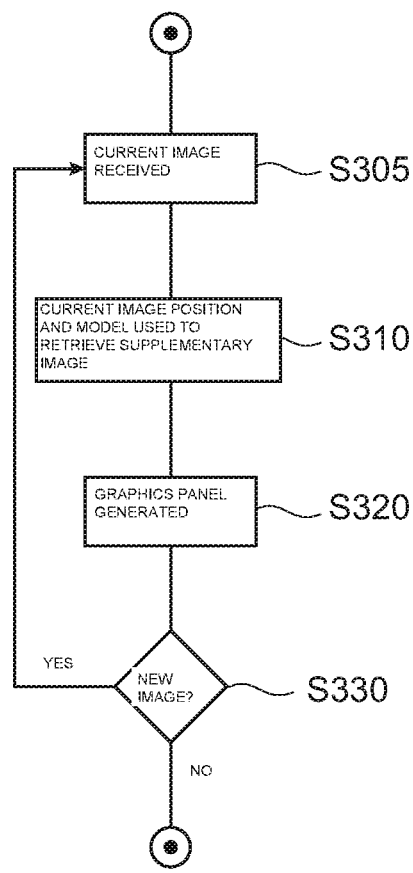
FIG. 2 shows a flow chart of a method for aiding in navigating a device in a network of tubular structures.

Flow chart in FIG. 2 summarizes the basic steps of the method as executed by apparatus 200.

In step S305 the current fluoroscopy image 190a and its projection direction is received.

In S310 a current image position of the footprint of the wire-guide and a generic vasculature model is used to retrieve the supplementary projection image from the sequence of previously acquired 2D angiographies 170a-c.

So retrieved supplementary image shows when displayed at least a partial footprint of the vasculature and affords a better view on the vasculature at the region of interest where the device is currently located than at least one angiography from among the sequence of angiographies when measured against goodness of view standard. The standard is selectable from a plurality of standards. A weighted average or any combination of the plurality of viewing standards may also be used.

In step S320, a graphics panel for display in a screen is generated.

The so generated graphics panel includes the current fluoroscopy image and the retrieved supplementary projection image In step S330 it is determined whether a new fluoro image has been received indicating that the guide wire has been advanced through the vasculature and has therefore changed its position in the imaged region of interest.

Upon receipt of a new fluoroscopy image, the apparatus is configured to repeat the above step S310 and then to update the graphics panel in step S330 to now include the newly received fluoro image along with a newly retrieved subsequent supplementary projection image.

According to one embodiment the step of retrieving the supplementary projection image includes the step of redefining the region of interest in the network is configured to use an identifier of that region to retrieve the supplementary image.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for aiding in navigating a device in a network of tubular structures, comprising:
an input configured to receive a current reference 2D projection image including a footprint of the device acquired at a first projection direction whilst the device is residing in the network of tubular structures;
a processor coupled to the input and configured to use a current in-image position of the footprint and a model of the network of tubular structures to retrieve, without using acquired 3D image data of the network of tubular structures, a supplementary projection image from a sequence of previously acquired 2D projection images, the so retrieved supplementary image showing, when displayed, at least a partial footprint of the network of tubular structures, the so retrieved supplementary image affording a view along a second projection direction on the network of tubular structures at a section of interest where the device currently resides;
a graphics display generator configured to generate for display on a screen a graphics panel including the current reference 2D projection image and the supplementary projection image, the apparatus configured to update the graphics panel upon receipt of a new projection image at the input, the updated panel then including the new projection image and a newly retrieved supplementary projection image, wherein the plurality of 2D projection images are previously acquired at different projection directions, wherein the processor is further configured to compute, based on the network model, a score for a first goodness of view standard from a plurality of standards or a combination of a plurality of different goodness of view standards, wherein the standard or any one of the standards accounts for any one of the following: (i) low degree of overlaps between the current reference 2D projection image in the part of the footprint and images of the sequence representing the section of interest, (ii) low degree of foreshortening of the part of the footprint representing the section of interest within the images of the sequence, (iii) high degree of tortuosity of the part of the footprint representing the section of interest within the images of the sequence, and the processor is further configured to select the supplementary image from among the sequence, based on the score for the goodness of view standard for each of the sequence.

2. The apparatus of claim 1, wherein the processor is further configured to retrieve, along with the supplementary image, a reference supplementary image having substantially the same projection direction as the current reference 2D projection image, the reference supplementary projection image affording a better view on the network of tubular structures at the section of interest than the current reference 2D projection image when measured against the first goodness of view standard, the supplementary image and the reference supplementary image thereby together affording complimentary views on the section of interest.

3. The apparatus of claim 1, wherein the processor is further configured to retrieve, along with the supplementary image, a further supplementary image, the further supplementary image affording a better view on the network of tubular structures at the section of interest than the supplementary image when measured against a second goodness of view standard different from the first goodness of view standard, the two supplementary images thereby together affording complimentary views on the section of interest.

4. The apparatus of claim 3, wherein the second goodness of view standard accounts for: (iv) angular closeness of the projection direction of the supplementary projection image to the projection direction of the further supplementary projection image or angular closeness of the projection direction of the supplementary projection image to the projection direction of the newly retrieved supplementary projection image.

5. The apparatus of claim 1, wherein the graphics display generator is further configured to generate annotation information for display on the panel, the annotation information including at least one of the computed score for the goodness of view standard of the supplementary image and one or more objective parameters used for the computation of the score.

6. The apparatus of claim 1, wherein the network of tubular structures is capable of assuming different shapes over the course of time, wherein the network model of tubular structures is one from a collection of different network models of tubular structures each corresponding to one of the different shapes, and wherein the processor is further configured to select the network model of tubular structures to correspond to the shape of the network of tubular structures at acquisition time of the current reference 2D projection image.

7. The apparatus of claim 1, wherein the graphics display generator is further configured to use the current in-image position of the device to overlay a graphic representation of the device at a corresponding position in the supplementary projection image as included in the graphics panel or is configured to overlay on the reference projection image a graphic representation of the region of interest as shown in the supplementary projection image.

8. The apparatus of claim 1, wherein the graphics display generator is further configured to color code the region of interest in the supplementary projection image as included in the graphics panel.

9. The apparatus of claim 1, wherein the device is a medical navigating device and the network of tubular structures is a coronary vasculature, the current 2D reference projection image is a fluoroscopy image of the navigating device residing in a coronary vessel of the coronary vasculature and the supplementary projection images are angiographies of the coronary vasculature.

10. A method of aiding in navigating a device in a network of tubular structures, the method comprising acts of:
receiving a current 2D projection image including a footprint of the device acquired at a first projection direction whilst the device is residing in the network of tubular structures;
retrieving, using a current in-image position of the footprint and a model of the network of tubular structures without using acquired 3D image data of the network of tubular structures, a supplementary projection image from a sequence of previously acquired 2D projection images, showing, when displayed, at least a partial footprint of the network of tubular structures affording a view along a second projection direction on the network of tubular structures at the section of interest where the device currently resides;
generating for display on a screen a graphics panel including the current 2D projection image and the supplementary projection image; and
updating the graphics panel upon receipt of a new projection image, the updated panel then including the new projection image and a newly retrieved supplementary projection image, wherein the plurality of 2D projection images previously are acquired at different projection directions, the method further comprising an act of computing, based on the network model, a score for a first goodness of view standard or a weighted combination of a plurality of different goodness of view standards, wherein the standard or any one of the standards accounts for any one of the following: (i) low degree of overlaps between the current 2D projection image in the part of the footprint and images of the sequence representing the section of interest, (ii) low degree of foreshortening of the part of the footprint representing the section of interest within the images of the sequence, (iii) high degree of tortuosity of the part of the footprint representing the section of interest, wherein the act of retrieving comprises an act of selecting the supplementary image from among the sequence, based on the score for the goodness of view standard for each of the sequence.

11. The method of claim 10, further comprising an act of:
retrieving along with the supplementary image a further supplementary image, the further supplementary image affording a better view on the network of tubular structures at the section of interest than the supplementary image when measured against a second goodness of view standard different from the first goodness of view standard, the two supplementary images thereby together affording complimentary views on the section of interest.

12. An X-ray imager support system comprising:
a database holding the 2D supplementary projection images;
the apparatus according to claim 1;
the X-ray imager;
the screen.

13. A computer-readable storage-memory that is not a transitory propagating wave or signal having stored thereon a computer program that configures a processor to perform a method for aiding in navigating a device in a network of tubular structures, the method including acts of:
retrieving, without using acquired 3D image data of the network of tubular structures, a supplementary projection image from a sequence of previously acquired 2D projection images using a current in-image position of the footprint and a model of the network of tubular structures, the so retrieved supplementary image showing, when displayed, at least a partial footprint of the network of tubular structures, the so retrieved supplementary image affording a view along a second projection direction on the network of tubular structures at a section of interest where the device currently resides, wherein the plurality of 2D projection images are previously acquired at different projection directions;
computing, based on the network model, a score for a first goodness of view standard from a plurality of standards or a combination of a plurality of different goodness of view standards, wherein the standard or any one of the standards accounts for any one of the following: (i) low degree of overlaps between the current reference 2D projection image in the part of the footprint and images of the sequence representing the section of interest, (ii) low degree of foreshortening of the part of the footprint representing the section of interest within the images of the sequence, (iii) high degree of tortuosity of the part of the footprint representing the section of interest within the images of the sequence;
selecting the supplementary image from among the sequence, based on the score for the goodness of view standard for each of the sequence; and
displaying the supplementary image.

14. A computer readable medium that is not a transitory propagating wave or signal having stored thereon a computer program that when executed by a processor configures the processor to perform acts of:
receiving a current 2D projection image including a footprint of the device acquired at a first projection direction whilst the device is residing in the network of tubular structures;
retrieving, using a current in-image position of the footprint and a model of the network of tubular structures without using acquired 3D image data of the network of tubular structures, a supplementary projection image from a sequence of previously acquired 2D projection images, showing when displayed, at least a partial footprint of the network of tubular structures affording a view along a second projection direction on the network of tubular structures at the section of interest where the device currently resides;
generating for display on a screen a graphics panel including the current 2D projection image and the supplementary projection image; and
updating the graphics panel upon receipt of a new projection image, the updated panel then including the new projection image and a newly retrieved supplementary projection image, wherein the plurality of 2D projection images are previously acquired at different projection directions, wherein the processor is further configured to compute, based on the network model, a score for a first goodness of view standard from a plurality of standards or a combination of a plurality of different goodness of view standards, wherein the standard or any one of the standards accounts for any one of the following: (i) low degree of overlaps between the current reference 2D projection image in the part of the footprint and images of the sequence representing the section of interest, (ii) low degree of foreshortening of the part of the footprint representing the section of interest within the images of the sequence, (iii) high degree of tortuosity of the part of the footprint representing the section of interest within the images of the sequence, and the processor is further configured to select the supplementary image from among the sequence, based on the score for the goodness of view standard for each of the sequence.

* * * * *